US012778628B2

(12) United States Patent
Parent

(10) Patent No.: US 12,778,628 B2
(45) Date of Patent: Nov. 3, 2026

(54) MEDICAL DEVICE FOR CARPAL TUNNEL RELEASE SURGERY

(71) Applicant: Protex Surgical, LLC, St. Petersburg, FL (US)

(72) Inventor: Thomas Parent, St. Petersburg, FL (US)

(73) Assignee: Protex Surgical, LLC, St. Petersburg, FL (US)

(*) Notice: Subject to any disclaimer, the term of this patent is extended or adjusted under 35 U.S.C. 154(b) by 170 days.

(21) Appl. No.: 18/748,245

(22) Filed: Jun. 20, 2024

(65) Prior Publication Data

US 2025/0064481 A1 Feb. 27, 2025

Related U.S. Application Data

(60) Provisional application No. 63/578,004, filed on Aug. 22, 2023.

(51) Int. Cl.
*A61B 17/34* (2006.01)
*A61B 17/32* (2006.01)

(52) U.S. Cl.
CPC .. *A61B 17/3423* (2013.01); *A61B 17/320036* (2013.01); *A61B 17/3494* (2013.01); *A61B 2017/320056* (2013.01); *A61B 2017/3445* (2013.01)

(58) Field of Classification Search
CPC ........ A61B 17/320036; A61B 17/3423; A61B 17/3494; A61B 2017/320056; A61B 2017/3445
See application file for complete search history.

(56) References Cited

U.S. PATENT DOCUMENTS

| | | | | |
|---|---|---|---|---|
| 5,273,024 | A * | 12/1993 | Menon ........... | A61B 17/320036 600/114 |
| 5,730,749 | A | 3/1998 | Battenfield | |
| 6,179,852 | B1 | 1/2001 | Strickland et al. | |
| 7,918,784 | B2 | 4/2011 | Wellborn et al. | |
| 8,273,098 | B2 | 9/2012 | Strickland | |
| 8,523,892 | B2 | 9/2013 | Rehnke et al. | |
| 8,672,960 | B2 | 3/2014 | Briganti et al. | |
| 8,992,424 | B2 | 3/2015 | Orbay et al. | |
| 9,254,122 | B2 | 2/2016 | Diao et al. | |

(Continued)

FOREIGN PATENT DOCUMENTS

WO 2022232582 A1 11/2022

*Primary Examiner* — Mohamed G Gabr
(74) *Attorney, Agent, or Firm* — Mark Terry

(57) ABSTRACT

A medical device for carpal tunnel release surgery includes an elongated element configured for insertion into a carpal tunnel region of the patient's wrist via an incision, an exposed groove extending via a longitudinal axis of the elongated element, the groove being configured for accommodating a light endoscope and a scalpel device for severing the patient's transverse carpal ligament, a flange extending outwards from, and co-extensive with, an entire rim of the groove, the flange comprising a flat plate configured for preventing the patient's medial nerve from entering the groove during the surgery, a top cover of the groove located at the proximal end of the device; and an orifice in the proximal end of the device that extends through the top cover and provides access to the groove, the orifice configured for insertion of the light endoscope and the scalpel device.

20 Claims, 9 Drawing Sheets

(56) References Cited

U.S. PATENT DOCUMENTS

| | | | | |
|---|---|---|---|---|
| 9,592,071 | B2 | 3/2017 | Berger | |
| 11,033,291 | B2 | 6/2021 | Bright | |
| 11,147,584 | B2 | 10/2021 | Seymour et al. | |
| 11,596,430 | B2 | 3/2023 | Mirza et al. | |
| 2009/0048620 | A1 | 2/2009 | Weiss et al. | |
| 2010/0049200 | A1* | 2/2010 | Re | A61B 17/1714 606/86 R |
| 2010/0069944 | A1* | 3/2010 | Murakami | A61B 17/00008 606/184 |
| 2014/0249558 | A1 | 9/2014 | McCormack et al. | |
| 2015/0320436 | A1* | 11/2015 | Agee | A61B 1/00087 600/104 |
| 2022/0054160 | A1 | 2/2022 | Bernal et al. | |
| 2022/0219657 | A1 | 7/2022 | Legay et al. | |
| 2023/0200833 | A1 | 6/2023 | Paterson | |

* cited by examiner

MEDICAL DEVICE FOR CARPAL TUNNEL RELEASE SURGERY

CROSS-REFERENCE TO RELATED APPLICATIONS

This patent application claims priority to provisional patent application No. 63/578,004 filed Aug. 22, 2023 and titled Medical Device for Carpal Tunnel Release Surgery. The subject matter of patent application No. 63/578,004 is hereby incorporated by reference in its entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The technical field relates generally to the field of surgical instruments and, more specifically, relates to the field of surgical instruments used for carpal tunnel release surgery.

BACKGROUND

Carpal tunnel syndrome (CTS) is a prevalent medical condition affecting millions globally, which results from the compression of the median nerve as it traverses the carpal tunnel in the wrist. This compression often leads to symptoms such as pain, numbness, tingling, and muscle weakness in the affected hand, particularly in the thumb and first three fingers. Traditional treatments have ranged from wrist splinting and anti-inflammatory medications to corticosteroid injections. However, when these conservative methods fail to alleviate symptoms or when the condition becomes severe, surgical intervention becomes necessary.

Carpal tunnel release surgery is the definitive treatment for CTS, aiming to relieve the pressure on the median nerve by severing the transverse carpal ligament. Two primary techniques are predominantly utilized: open release surgery and endoscopic release. The open release method involves a larger incision in the palm and wrist, providing direct visualization and access to the ligament. In contrast, the endoscopic method utilizes smaller incisions and a camera to guide the surgeon. Both techniques have their advantages and challenges. However, there remains a persistent need in the medical community to enhance the precision, reduce invasiveness, and expedite the recovery associated with carpal tunnel release surgeries.

One of the paramount concerns in carpal tunnel release surgery is the potential damage to the median nerve. While the primary objective of this procedure is to alleviate pressure on the median nerve by cutting the transverse carpal ligament, the surgery itself poses risks. Given the close proximity of the ligament to the nerve, inadvertent nicks or cuts can occur, especially if there is significant swelling or anatomical variances. Damage to the median nerve during the operation can exacerbate the symptoms of carpal tunnel syndrome or introduce new complications, such as persistent pain, loss of sensation, or motor function impairment. Such inadvertent mistakes can prolong the patient's recovery time, diminish the overall success rate of the surgery, and can sometimes necessitate additional surgical interventions or long-term therapeutic measures. Thus, ensuring the safety and precision of the carpal tunnel release procedure is of utmost importance for both patients and practitioners.

Therefore, a need exists to overcome the problems with the prior art as discussed above, and particularly for a more accurate, efficient and safe way of performing carpal tunnel release surgery.

SUMMARY

A medical device for carpal tunnel release surgery is provided. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a medical device for carpal tunnel release surgery is provided that solves the above-described problems. The medical device for carpal tunnel release surgery includes an elongated element configured for insertion into a carpal tunnel region of the patient's wrist via an incision, an exposed groove extending via a longitudinal axis of the elongated element, the groove being configured for accommodating a light endoscope and a scalpel device for severing the patient's transverse carpal ligament, a flange extending outwards from, and co-extensive with, an entire rim of the groove, the flange comprising a flat plate configured for preventing the patient's medial nerve from entering the groove during the surgery, a top cover of the groove located at the proximal end of the device; and an orifice in the proximal end of the device that extends through the top cover and provides access to the groove, the orifice configured for insertion of the light endoscope and the scalpel device. In one embodiment, the medical device for carpal tunnel release surgery further comprises a barrier located at a distal end of the elongated element that terminates the groove, such that any instrument inserted into the groove cannot move past the barrier.

BRIEF DESCRIPTION OF THE DRAWINGS

The accompanying drawings, which are incorporated in and constitute a part of this disclosure, illustrate various example embodiments. In accordance with common practice the various features illustrated in the drawings may not be drawn to scale. Accordingly, the dimensions of the various features may be arbitrarily expanded or reduced for clarity. In addition, some of the drawings may not depict all of the components of the given system, method or apparatus. In the drawings.

DETAILED DESCRIPTION

Figure 1:
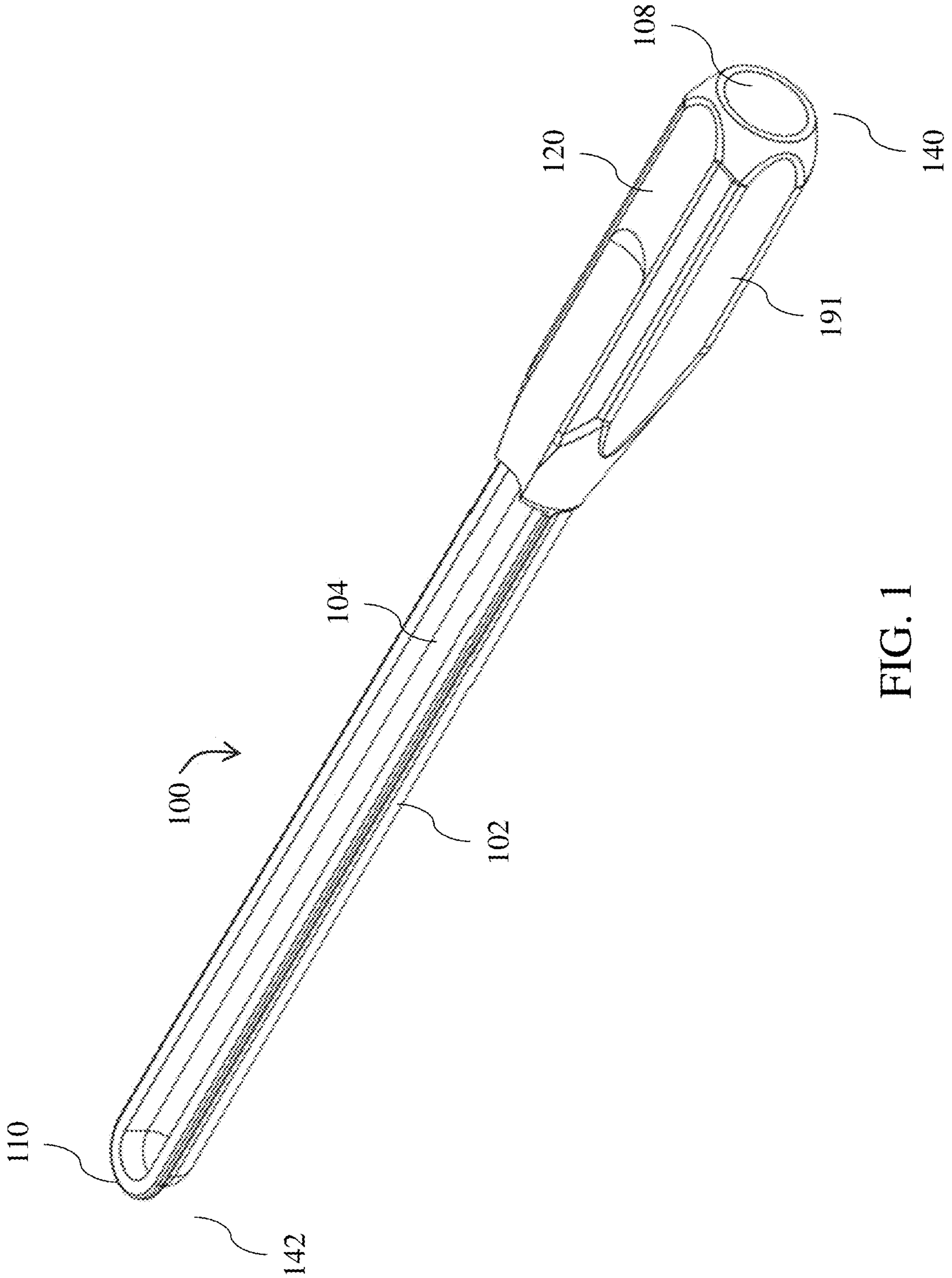
FIG. 1 depicts a rear perspective view of a medical device for carpal tunnel release surgery, according to an embodiment.
Figure 2:
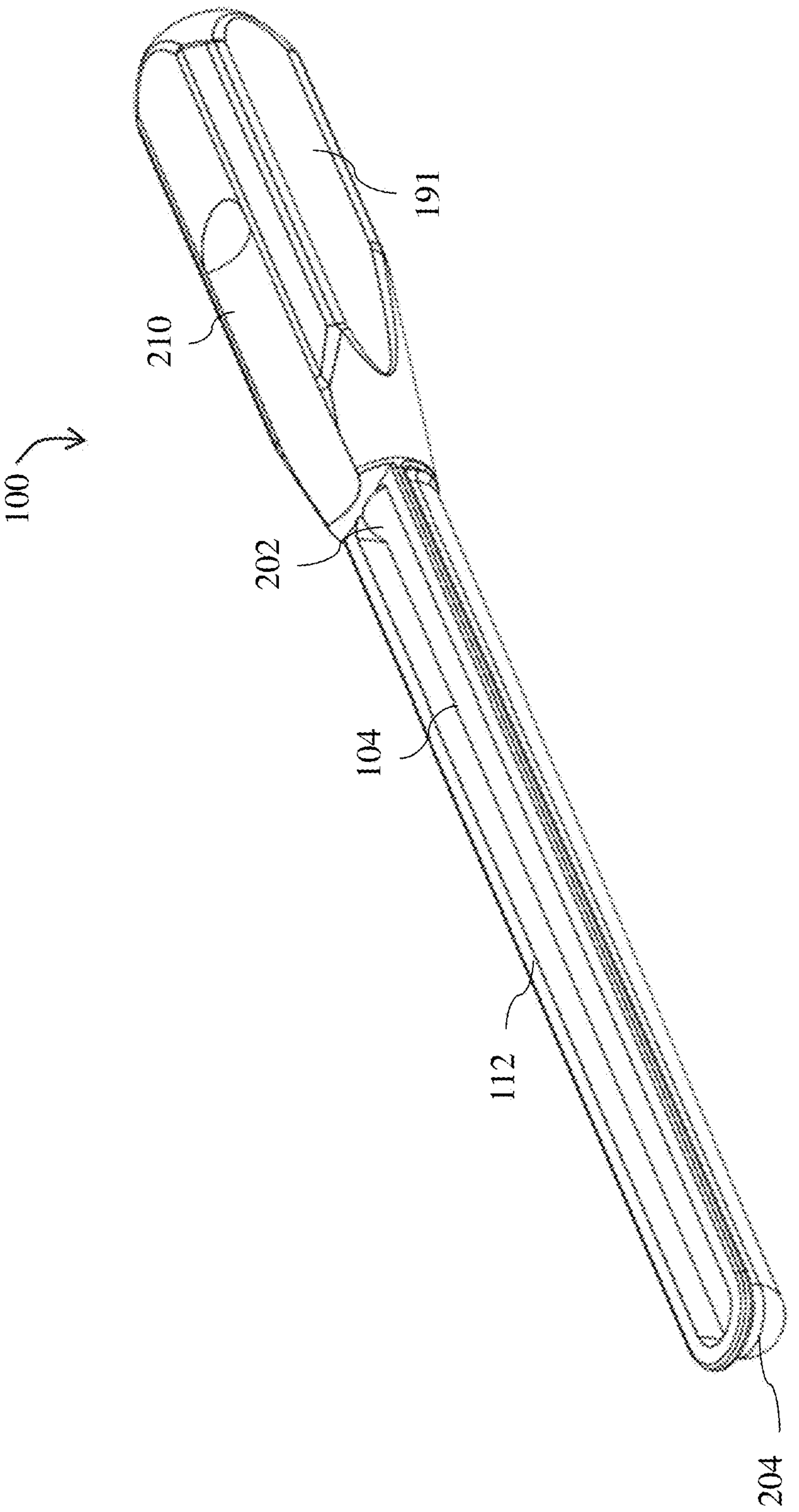
FIG. 2 depicts a front perspective view of the medical device for carpal tunnel release surgery, according to an embodiment.

The following detailed description refers to the accompanying drawings. Wherever possible, the same reference numbers are used in the drawings and the following description to refer to the same or similar elements. While embodiments of the claimed subject matter may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the claimed subject matter. Instead, the proper scope of the claimed subject matter is defined by the appended claims.

The claimed subject matter improves over the prior art by providing a medical device for carpal tunnel release surgery with enhanced precision, a reduction in invasiveness, increased safety and expedited the recovery associated with carpal tunnel release surgeries. The claimed subject matter presents an inexpensively manufactured and easy to use medical device for carpal tunnel release surgery that reduces or eliminates the possibility that the median nerve is damaged to severed during said surgery. This feature increases the safety of carpal tunnel release surgery and results in saved time, effort, expenses and morbidity.

The accompanying drawings, which are incorporated in and constitute a part of this disclosure, illustrate various example embodiments. The claimed medical device for carpal tunnel release surgery will now be described with respect to FIGS. 1 through 9.

A medical device for carpal tunnel release surgery 100 includes an elongated element 102, which may be a shaft, configured for insertion into a carpal tunnel region of the patient's wrist via an incision, the elongated element including an exposed groove 104 extending via a longitudinal axis of the elongated element, the groove being configured for accommodating a light endoscope and a scalpel device for severing the patient's transverse carpal ligament. The device 100 also includes a flange 110 extending outwards from, and co-extensive with, an entire rim 112 of the groove, the flange comprising a flat plate configured for preventing the patient's medial nerve from entering the groove during the surgery. The device 100 also includes a top cover 120 of the groove located at the proximal end 140 of the device 100. The device 100 further includes an orifice 108 in the proximal end 140 of the device that extends through the top cover and provides access to the groove, the orifice configured for insertion of the light endoscope, the scalpel device, and other devices.

Figure 3:
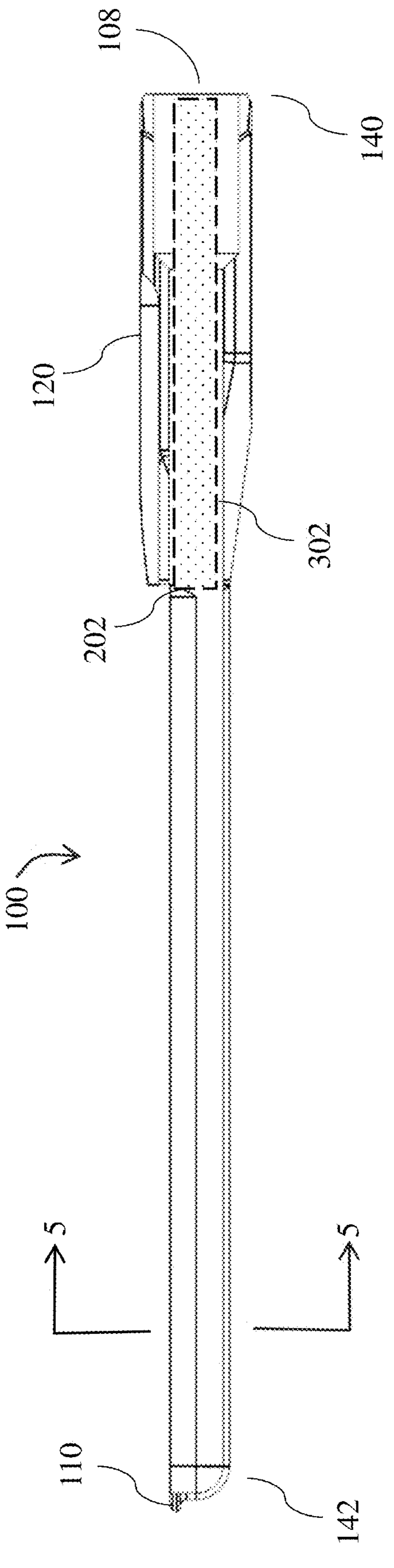
FIG. 3 depicts a side cross-sectional view of the medical device for carpal tunnel release surgery, according to an embodiment.

The device 100 may further include a barrier 204 located at a distal end 142 of the elongated element that terminates the groove 104 such that any instrument inserted into the groove cannot move past the barrier. The barrier may be semicircular shaped, as seen in FIG. 3. Also, the groove 104 may further include a gutter having a semi-circular cross section, as shown in FIG. 5.

Figure 5:
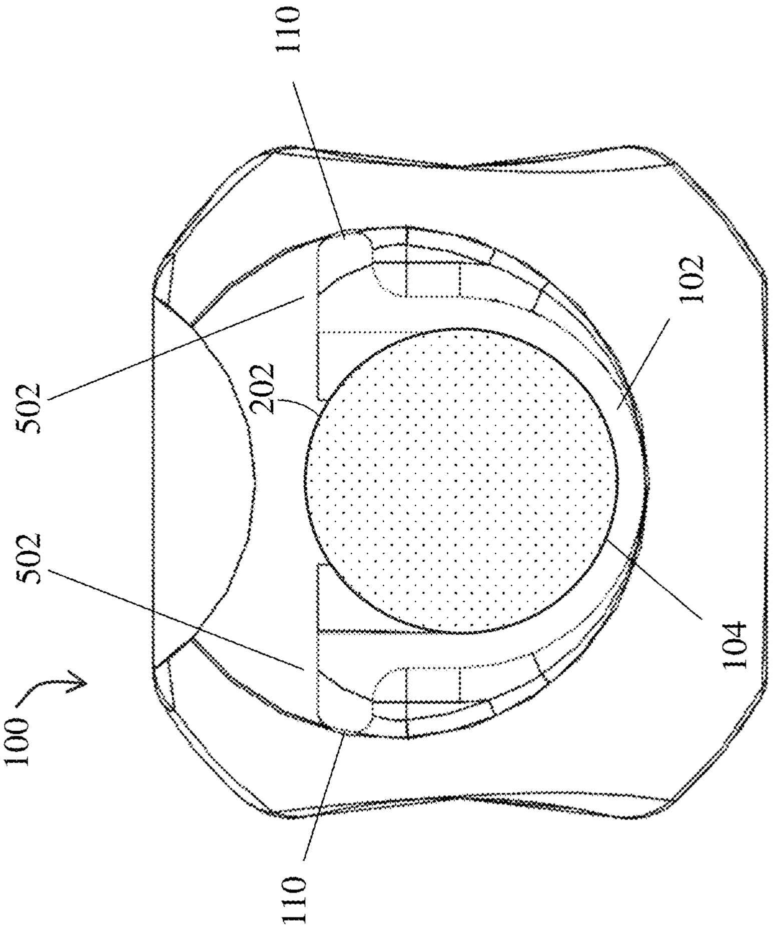
FIG. 5 depicts a front cross-sectional view of the medical device for carpal tunnel release surgery, according to an embodiment.

The device 100 also includes a flange 110 extending outwards from, and co-extensive with, an entire rim 112 of the groove, the flange 110 shown as extending outwards in opposite directions in FIG. 5, and the flange 110 shown as extending outwards in the distal direction in front of the groove in the front tip of the device in FIG. 3. Further, an entirety of the top surface 502 of the flange 110 may be co-planar. And an entirety of the bottom surface of the flange 110 may be co-planar.

Also, the top cover 120 may further comprise a portion of material that covers the top of the groove 104 at the proximal end 140 of the device. Access is granted to the space under the top cover 120 via the rear orifice 108 and via the front facing orifice 202. Further, a groove 210 may be located on the top surface of the top cover 120. Said groove 210 facilitates manual manipulation of the device 100 during surgery, such that better purchase on the device is provided via said groove. Also, a groove 191 may be located on the left-side surface of the proximal end 140 of the device 100, and a matching groove 192 on the right-side surface. Said grooves 191, 192 also facilitate manual manipulation of the device 100 during surgery, such that better purchase on the device is provided via said grooves.

Figure 4:
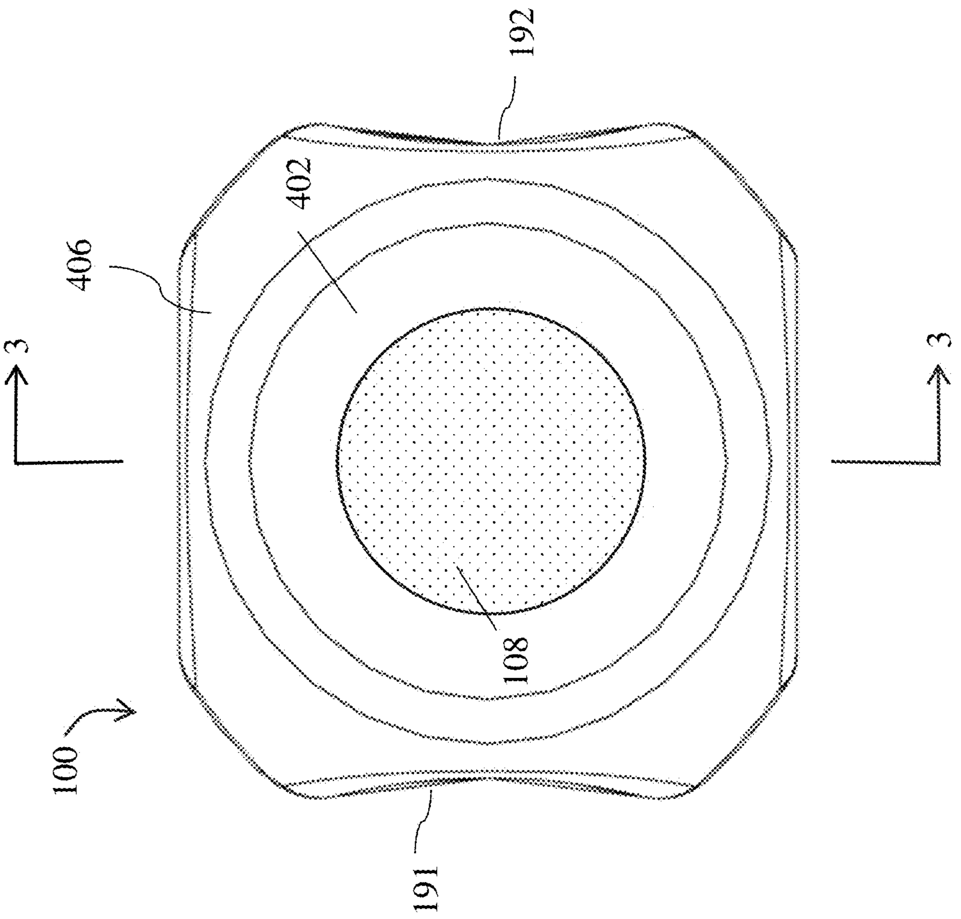
FIG. 4 depicts a rear view of the medical device for carpal tunnel release surgery, according to an embodiment.

The orifice 108 and orifice 202 in the proximal end 140 of the device are colinear with the groove. See FIG. 3 which shows an outline 302 representing how the orifice 108 and orifice 202 are colinear with, and provides access to, the groove 104. Outline 302 represents a void or hole in the interior of device 100. The orifice 108 in the proximal end 140 of the device 100 is configured to allow for the insertion of the light endoscope, the scalpel device and other instruments from a proximal direction (from proximal end 140) and towards a distal direction (towards distal end 142). The orifice 108 may be surrounded by a bevel 402 in the rear-facing or proximal-direction facing vertical surface 406 of the device 100. Further, the rear-facing or proximal-direction facing vertical surface 406 of the device 100 may be substantially square or rectangular shaped with corners being rounded or truncated, as shown in FIG. 4.

Figure 6:
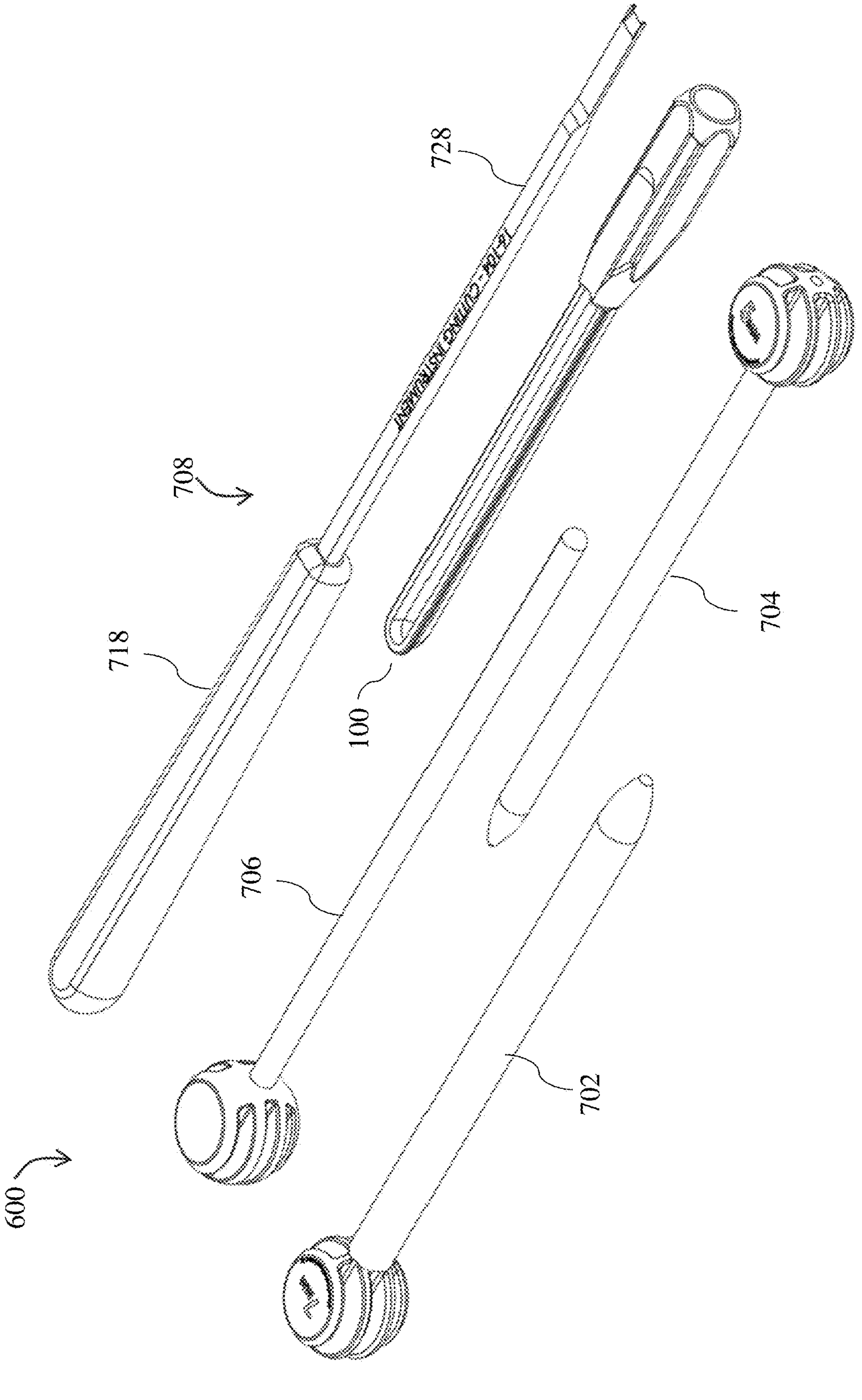
FIG. 6 depicts a top perspective view of a kit for carpal tunnel release surgery including the claimed medical device, according to an embodiment.
Figure 7:
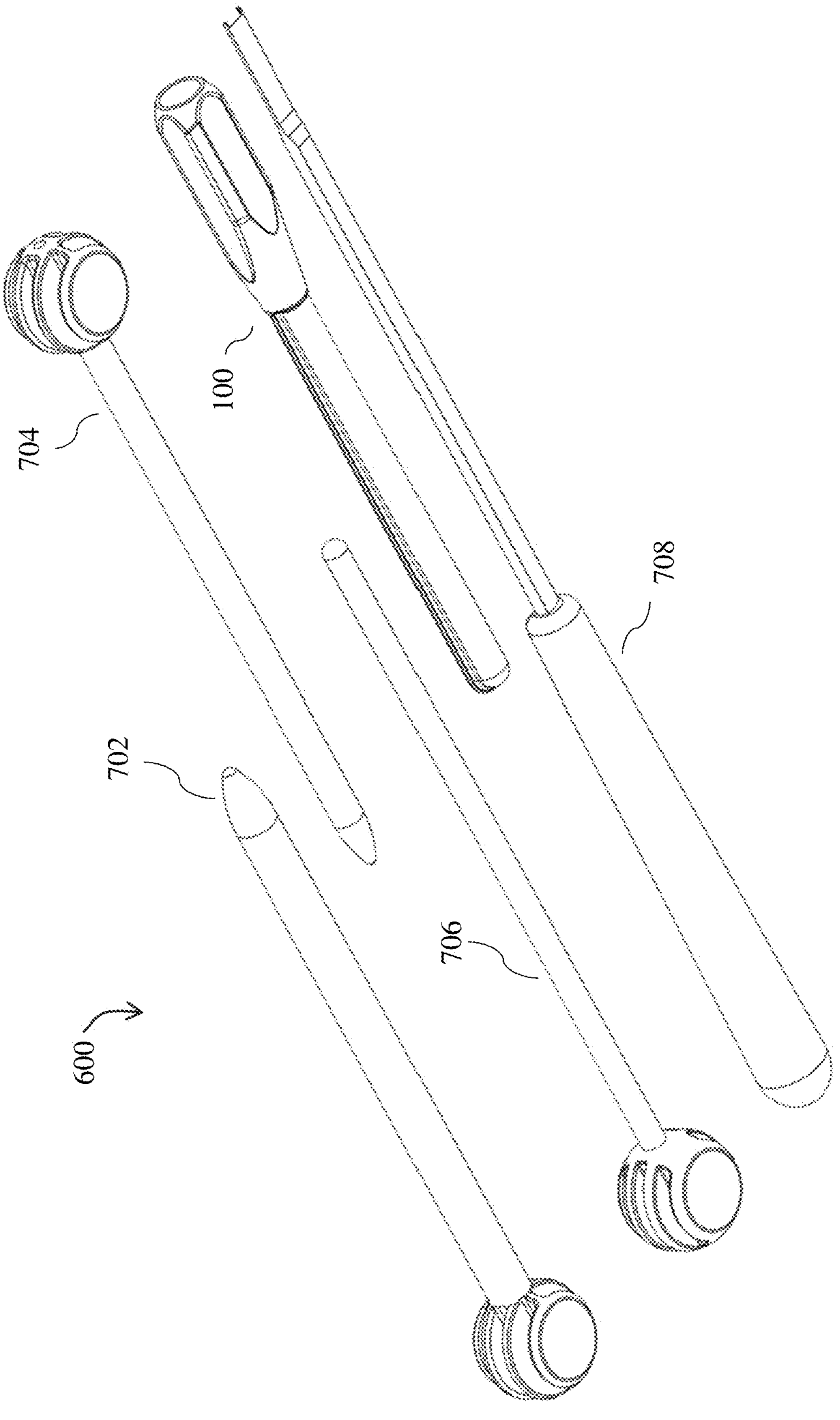
FIG. 7 depicts a bottom perspective view of the kit for carpal tunnel release surgery including the claimed medical device, according to an embodiment.

FIGS. 6 and 7 depict top and bottom perspective views of a kit 600 for carpal tunnel release surgery including the claimed medical device 100, according to an embodiment. FIGS. 6 and 7 show the kit 600 also includes spacer elements 702, 704, 706 for insertion into device 100 via the orifice 108 in the proximal end of the device 100 from a proximal direction (from proximal end 140) and towards a distal direction (towards distal end 142). FIGS. 6 and 7 show the kit also includes a scalpel device 708 for insertion into device 100 via the orifice 108 in the proximal end of the device 100 from a proximal direction (from proximal end 140) and towards a distal direction (towards distal end 142). The scalpel device 708 comprises a handle 718 attached to a shaft 728 that includes a scalpel on its distal tip, wherein the scalpel is configured for cutting the transverse carpal ligament.

The claimed device 100 and/or kit 600, and/or any of its components, may be composed of stainless steel, such as the 316L variety, which is known for its high corrosion resistance and impressive strength. This grade of stainless steel offers increased biocompatibility, ensuring minimal risk of adverse reactions when in contact with the human body. This grade of stainless steel also offers ease of sterilization.

The claimed device 100 and/or kit 600, and/or any of its components, may be composed of titanium, and its range of alloys, due to their high strength-to-weight ratio, as well as being both lightweight and sturdy. Titanium's inherent non-magnetic properties make it especially suitable when used alongside MRI machines or other electromagnetic equipment. Additionally, titanium has robust resistance to corrosion and the ability to seamlessly integrate with the human body.

The claimed device 100 and/or kit 600, and/or any of its components, may be composed of nitinol, a nickel-titanium alloy, due to its enhanced flexibility and the ability to return to its original shape after deformation. Nitinol offers shape-memory and super-elastic characteristics, being adaptable to intricate surgical maneuvers, and providing the surgeon with more control and precision.

The claimed device 100 and/or kit 600, and/or any of its components, may be composed of medical-grade plastics or silicones, since these materials can be molded into complex shapes and structures, providing ergonomic benefits or catering to single-use requirements. Polymers like PEEK (Polyether ether ketone) are particularly noteworthy due to their biocompatibility, mechanical strength, and stability. Also, the use of plastics would render the claimed device 100 and/or kit 600 disposable.

Figure 8:
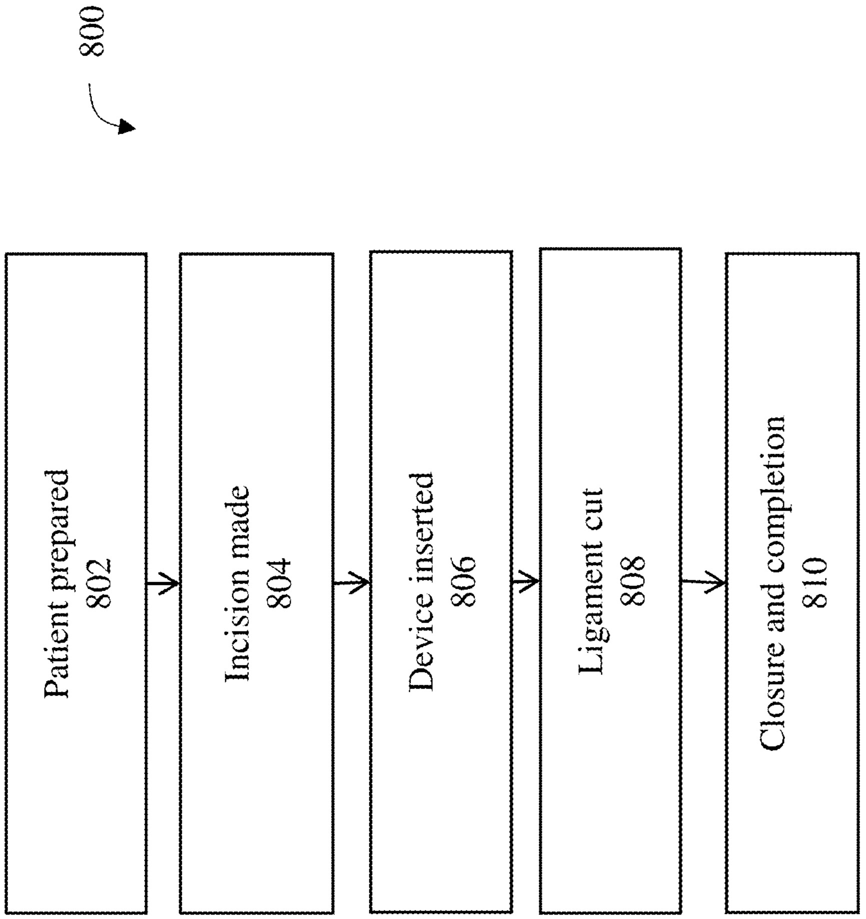
FIG. 8 depicts a flowchart describing the use of the kit for carpal tunnel release surgery, according to one embodiment.

FIG. 8 depicts a flowchart 800 describing the use of the kit 600 for carpal tunnel release surgery, according to one embodiment. The steps described in FIG. 8 are provided in relation to the diagram of FIG. 9, which depicts a diagram showing the use of the kit during carpal tunnel release surgery. Carpal tunnel release surgery begins in step 802 with preparation of the patient, including any necessary cleaning and sterilization of the surgical area, and the administering of a local anesthetic to numb the wrist and hand 900, though in some cases, regional or general anesthesia may be used. In step 804, the surgeon makes a small incision 910 in the palm of the hand near the wrist, aligning it with the carpal tunnel.

Figure 9:
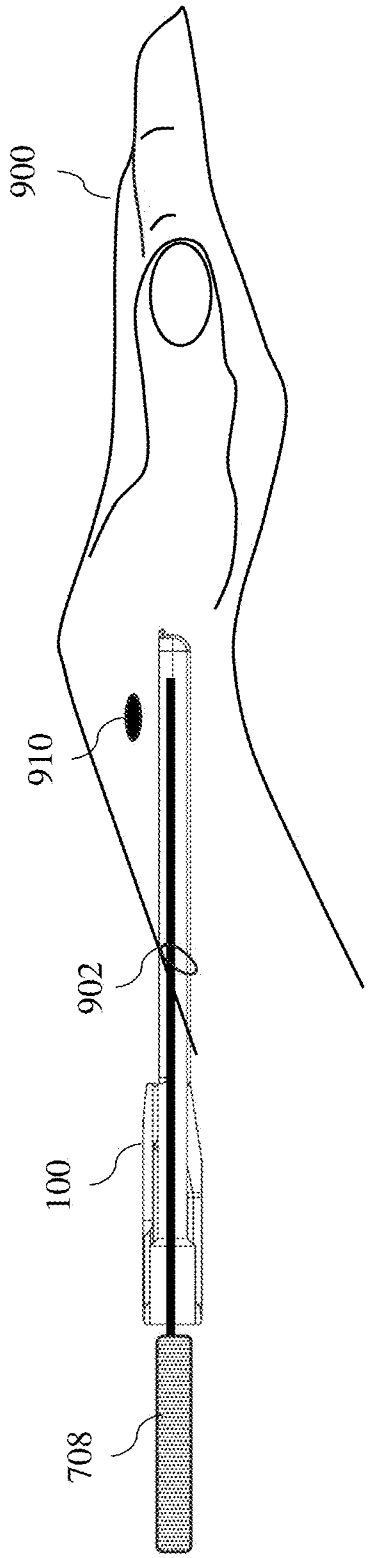
FIG. 9 depicts a diagram showing the use of the kit during carpal tunnel release surgery, according to one embodiment.

In step 806, through the incision 902, the device 100 is inserted in a distal direction (towards the right in FIG. 9) such that the transverse carpal ligament 910 (shown in cross section in FIG. 9), which forms the roof of the carpal tunnel, is located near the distal end 142 of the device 100. FIG. 9 shows the desired location of the device 100 during the carpal tunnel release surgery. In step 808, spacer devices 702, 704, 706 may be inserted into the device 700 via the orifice 108 so as to make room for subsequent tools and devices. Also, an endoscope may be inserted into the device 700 via the orifice 108 so as to view the ligament 910. Then, the shaft 728 of the scalpel device 708 is inserted into the device 700 via the orifice 108 until the scalpel on the distal tip of the shaft reaches near the end of the groove 104 of the device 100, such that the scalpel is located under the transverse carpal ligament 910. Subsequently, the scalpel device 708 is maneuvered to carefully cut the transverse carpal ligament 910 to relieve pressure on the median nerve. Care is taken to avoid damage to surrounding structures such as tendons and nerves.

After the ligament is cut, in step 810, the surgeon may inspect the carpal tunnel for any additional anomalies or issues that need addressing. Once satisfied with the decompression, the incision 902 is closed with sutures, the wound is dressed, and the hand is bandaged to protect the area and manage swelling.

Recall the device 100 has a flange 110 that is specific to keeping the medial nerve underneath and below the top surface of the flange, so as to prevent any nicks or cuts into this nerve. Said flange 110 forces the nerve below the horizon of the device 100 to prevent damage.

Further, the device 100 may be composed of a water clear material with a high polish that exhibits optical clarity for improved visualization. To improve visualization of the medial nerve adjacent to the device 100 during use and to confirm said nerve is safe from nicks and cuts is a crucial feature of the claimed embodiments. Said optical clarity will also allow the surgeon to take images of the medial nerve and keep said images on record if ever there is an adjudication of a claim made against a performed carpal tunnel procedure. Said water clear device 100 offers an unprecedented advantage to surgeons who desire verification that the medial nerve was safe during the entire surgical procedure. The device 100 in a water clear form allows the surgeon proper visualization to have this verification on record for future use if needed.

The device 100 may also be configured to become a light pipe to improve visualization of the surgical environment, such that an endoscopic light source need not be inserted into the surgical field during the surgical procedure. A less cluttered surgical space improves the workspace for the surgeon to perform the surgical procedure. A light source may be attached to the device 100 external to the surgical field since the light would be piped directly into the surgical site for visualization purposes via the device 100.

Embodiments may be described above with reference to functions or acts, which comprise methods. The functions/acts noted above may occur out of order as shown or described. For example, two functions/acts shown or described in succession may in fact be executed substantially concurrently or the functions/acts may sometimes be executed in the reverse order, depending upon the functionality/acts involved. While certain embodiments have been described, other embodiments may exist. Further, the disclosed methods' functions/acts may be modified in any manner, including by reordering functions/acts and/or inserting or deleting functions/acts, without departing from the spirit of the claimed subject matter.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A medical device for carpal tunnel release surgery in a patient, the device comprising:

a) an elongated element configured for insertion into a carpal tunnel region of the patient's wrist via an incision, the elongated element having a distal end;

b) an exposed groove extending via a longitudinal axis of the elongated element, the groove being configured for accommodating a light endoscope and a scalpel device for severing the patient's transverse carpal ligament;

c) a flange extending outwards from, and co-extensive with, an entire rim of the groove, the flange comprising a flat plate configured for preventing the patient's medial nerve from entering the groove during the surgery, the flange having a distal end that extends beyond the distal end of the elongated element;

d) a top cover of the groove located at the proximal end of the device; and e) an orifice in the proximal end of the device that extends through the top cover and provides access to the groove, the orifice configured for insertion of the light endoscope and the scalpel device.

2. The medical device of claim 1, further comprising a barrier located at a distal end of the elongated element that terminates the groove.

3. The medical device of claim 2, wherein the elongated element comprises a shaft.

4. The medical device of claim 3, wherein the groove comprises a gutter having a semi-circular cross section.

5. The medical device of claim 4, wherein an entirety of the top surface of the flange is co-planar.

6. The medical device of claim 4, wherein the top cover comprises a portion of material that covers a top of the groove at the proximal end of the device.

7. The medical device of claim 6, wherein the orifice in the proximal end of the device is colinear with the groove.

8. The medical device of claim 7, wherein the orifice in the proximal end of the device faces a proximal direction of the device.

9. The medical device of claim 8, wherein the orifice in the proximal end of the device is configured to allow for the insertion of the light endoscope and the scalpel device from a proximal direction and towards a distal direction.

10. The medical device of claim 9, wherein the medical device is composed of stainless steel.

11. A medical device for carpal tunnel release surgery in a patient, the device comprising:

a) an elongated element configured for insertion into a carpal tunnel region of the patient's wrist via an incision, the elongated element having a distal end;

b) an exposed groove extending via a longitudinal axis of the elongated element, the groove being configured for accommodating a light endoscope and a scalpel device for severing the patient's transverse carpal ligament, and a barrier located at a distal end of the elongated element that terminates the groove;

c) a flange extending outwards from, and co-extensive with, an entire rim of the groove, the flange comprising a flat plate configured for preventing the patient's medial nerve from entering the groove during the surgery, the flange having a distal end that extends beyond the distal end of the elongated element;

d) a top cover of the groove located at the proximal end of the device; and e) an orifice in the proximal end of the device that extends through the top cover and provides access to the groove, the orifice configured for insertion of the light endoscope and the scalpel device.

12. The medical device of claim 11, wherein the barrier comprises a semicircular wall.

13. The medical device of claim 12, wherein the elongated element comprises a shaft.

14. The medical device of claim 13, wherein the groove comprises a gutter having a semi-circular cross section.

15. The medical device of claim 14, wherein an entirety of the top surface of the flange is co-planar.

16. The medical device of claim 14, wherein the top cover comprises a portion of material that covers a top of the groove at the proximal end of the device.

17. The medical device of claim 16, wherein the orifice in the proximal end of the device is colinear with the groove.

18. The medical device of claim 17, wherein the orifice in the proximal end of the device faces a proximal direction of the device.

19. The medical device of claim 18, wherein the orifice in the proximal end of the device is configured to allow for the insertion of the light endoscope and the scalpel device from a proximal direction and towards a distal direction.

20. The medical device of claim 19, wherein the medical device is composed of stainless steel.

* * * * *